(12) United States Patent
Nielson (10) Patent No.: US 8,585,099 B2
(45) Date of Patent: Nov. 19, 2013

(54) SANITARY COUPLING ASSEMBLY

(75) Inventor: Jeffrey T. Nielson, Piscataway, NJ (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 18 days.

(21) Appl. No.: 12/552,785

(22) Filed: Sep. 2, 2009

(65) Prior Publication Data
US 2010/0059985 A1    Mar. 11, 2010

Related U.S. Application Data

(60) Provisional application No. 61/095,213, filed on Sep. 8, 2008.

(51) Int. Cl.
*F16L 33/00* (2006.01)

(52) U.S. Cl.
USPC .............................................. 285/247; 285/25

(58) Field of Classification Search
USPC ................................................ 285/245–251
See application file for complete search history.

(56) References Cited

U.S. PATENT DOCUMENTS

| | | | | | |
|---|---|---|---|---|---|
| 1,345,520 | A | * | 7/1920 | Vivarttas | 251/149 |
| 2,266,211 | A | * | 12/1941 | Kaiser | 285/247 |
| 2,360,761 | A | * | 10/1944 | Clickner | 285/251 |
| 2,399,791 | A | * | 5/1946 | Conroy | 285/251 |
| 2,783,809 | A | * | 3/1957 | Haines | 285/390 |
| 2,816,781 | A | * | 12/1957 | Woodling | 285/222.4 |
| 3,032,358 | A | * | 5/1962 | Rolston | 285/247 |
| 3,287,033 | A | * | 11/1966 | Currie | 285/40 |
| 3,316,369 | A | * | 4/1967 | Skinner | 200/61.58 R |
| 3,684,319 | A | * | 8/1972 | Samartina | 285/247 |
| 3,744,530 | A | * | 7/1973 | Perry | 138/145 |
| 4,198,079 | A | * | 4/1980 | Shah | 285/245 |
| 4,396,658 | A | * | 8/1983 | Mettes et al. | 428/35.8 |
| 4,411,435 | A | * | 10/1983 | McStravick | 277/336 |
| 4,413,247 | A | * | 11/1983 | Hire | 337/368 |
| 4,539,082 | A | * | 9/1985 | Klotz et al. | 205/517 |
| 4,613,443 | A | * | 9/1986 | Rao et al. | 508/138 |
| 4,878,285 | A | * | 11/1989 | Carstensen | 29/451 |
| 5,240,291 | A | * | 8/1993 | Zornow | 285/40 |
| 5,393,104 | A | * | 2/1995 | Zornow | 285/40 |
| 5,622,393 | A | * | 4/1997 | Elbich et al. | 285/245 |

(Continued)

FOREIGN PATENT DOCUMENTS

| | | |
|---|---|---|
| CN | 2114077 U | 8/1992 |
| CN | 2292956 Y | 9/1998 |
| JP | 01113689 U | 7/1989 |
| KR | 20-1999-0020410 U | 6/1999 |

OTHER PUBLICATIONS

PCT/US2009/055743 International Search Report and Written Opinion mailed Feb. 2, 2010 in PCT application corresponding to U.S. Appl. 12/552,785.

*Primary Examiner* — Aaron Dunwoody
(74) *Attorney, Agent, or Firm* — Abel Law Group, LLP; Chi Suk Kim (57) ABSTRACT

A sanitary coupling assembly for mounting on a fluid system includes a female coupler and a male coupler. The female coupler has a distal end and a proximal end. The distal end has a first inner threaded surface defining an opening therein to receive an end of a hose. The proximal end has a second inner threaded surface having a polymer coating. The proximal end is configured to matingly engage a complementary structure located on the male coupler.

19 Claims, 4 Drawing Sheets

(56) References Cited

U.S. PATENT DOCUMENTS

| | | | |
|---|---|---|---|
| 5,860,678 A * | 1/1999 | Urzua | 285/40 |
| 6,805,969 B2 * | 10/2004 | Pagilagan | 428/474.7 |
| 7,025,384 B2 * | 4/2006 | Whitehead et al. | 285/55 |
| 7,240,925 B2 * | 7/2007 | Fukano et al. | 285/247 |
| 7,267,372 B2 * | 9/2007 | Roberts et al. | 285/249 |
| 2004/0239110 A1 * | 12/2004 | Pedersen et al. | 285/255 |

* cited by examiner

SANITARY COUPLING ASSEMBLY

CROSS-REFERENCE TO RELATED APPLICATIONS

The present application claims priority from U.S. Provisional Patent Application No. 61/095,213, filed Sep. 8, 2008, entitled "SANITARY COUPLING ASSEMBLY," naming inventor Jeffrey T. Nielson, which application is incorporated by reference herein in its entirety.

FIELD OF THE DISCLOSURE

This disclosure, in general, relates to a coupler. More particularly, the disclosure relates to a sanitary coupling assembly.

BACKGROUND

Large-scale production of pharmaceuticals, fluids for use in medical applications, and food grade products relies on maintenance of sanitary environments. Exposure of such products to bacteria or contaminants results in a reduced quality and, in some cases, toxic byproducts. As such, food and medical product manufacturers attempt to reduce points of contamination and have turned to sanitary hoses and connectors as part of an effort to maintain a sanitary environment.

Couplers used for attachment to a hose provide a sealed conduit that is not susceptible to bacteria or other contaminants at the coupler connection. In the area of consumable bulk liquids, such as milk, consumable bulk powders and granular materials, such as dry powder milk, there is a need for minimizing the exposure of such bulk liquids, powders, and granular materials to bacteria or other contaminants. The industry has relied upon a steel barbed coupler attached with compression straps for hoses in applications transporting this type of bulk product. Other coupler designs have included a piece that conforms to the hose's inner surface to aid in sealing and maintaining sanitary conditions.

In part, manufacturers have turned to reusable couplers to couple flexible hoses. However, reusable couplers have a limited lifetime and have to fit a variety of hose diameters/sizes. Commercially available couplers typically need a variety of different sized couplers for a range of outer diameter variations of a hose. Typically, a particular inner diameter sized hose may have a number of outside diameters. For a particular inner diameter sized hose, greater than 3 or 4 different coupler sizes may be needed based on the inner diameter of the coupler and variations in the outside diameter of the hose. An incorrect match and lack of interference between the coupler inner diameter and the hose outside diameter results in a non-sanitary environment that is prone to contamination.

Further, problems occur with respect to galling of the threads on the couplers when they are matingly engaged. To alleviate this problem, manufacturers have designed polymer inserts that are chemically bonded to the proximal end of the female coupler. Unfortunately, bonding issues arise with the use of the separate polymer component. Issues also arise with the couplers locking up, damaging the polymer insert and making it difficult to disengage mated couplers.

As such, improved couplers would be desirable.

SUMMARY

In an embodiment, a sanitary coupler includes a distal end and a proximal end. The distal end has a first inner threaded surface defining an opening therein to receive an end of a hose. The proximal end has a second inner threaded surface having a polymer coating. The proximal end is configured to matingly engage a complementary structure located on a complementary coupler.

In another embodiment, a sanitary coupler includes a distal end and a proximal end. The distal end has a first inner threaded surface defining an opening therein to receive an end of a hose. The distal end has an interference between an outer diameter of the hose and an inner diameter of the first inner threaded surface at least about 0.030 inches and up to at least about 0.090 inches. The proximal end has a second inner threaded surface configured to matingly engage a complementary structure located on a complementary coupler.

In an exemplary embodiment, a sanitary coupling assembly for mounting on a fluid system includes a female coupler and a male coupler. The female coupler includes a distal end and a proximal end. The distal end has a first inner threaded surface defining an opening therein to receive an end of a hose. The proximal end has a second inner threaded surface defining an opening adjacent and coaxial with the opening of the distal end to form a passageway along a central axis of the female coupler allowing fluid communication therethrough. The second inner threaded surface has a polymer coating. The male coupler includes an end having an outer threaded surface configured to matingly engage the second inner threaded surface of the female coupler.

In an additional example, a fluid system includes a first fluid container coupled to a first inner threaded surface of a distal end of a female coupler. A proximal end of the female coupler includes a second inner threaded surface having a polymer coating. The fluid system further includes a second fluid container coupled to a distal end of a male coupler. A proximal end of the male coupler includes an outer threaded surface configured to matingly engage the second inner threaded surface of the female coupler.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION OF THE DRAWINGS

In an exemplary embodiment, a coupling assembly includes mating couplers that can be coupled together and to various fluid conduit systems to provide a fluid path between the fluid systems. The coupling assembly provides a sanitary environment for fluid to flow between containers or conduits and prevents contaminants from entering the fluid path.

In an embodiment and as illustrated in FIGS. 1, 2, 3, and 4, the coupling assembly includes two couplers, female coupler 100 and male coupler 200. When the female coupler 100 and the male coupler 200 are coupled, the female coupler 100 and male coupler 200 are configured to matingly engage to define a fluid passage through the coupling assembly. For directional orientation, each coupler (100 and 200) has a proximal end illustrated nearest the opposing connector and a distal end illustrated furthest from the opposing connector. The proximal ends of the female coupler 100 and male coupler 200 are dimensioned to matingly engage. In an embodiment, the female coupler 100 has an inside diameter and the male coupler 200 has an outside diameter wherein the inside diameter of the female coupler 100 is greater than the outside diameter of the male coupler 200 to provide a frictional fit.

The female coupler 100 includes a proximal end 102 and a distal end 104. The distal end 104 includes a first inner threaded surface 106 that defines an opening 108 for receiving an end of a hose 300. The proximal end 102 of the female coupler 100 further includes a second threaded surface 110 that defines an opening 112 adjacent and coaxial with the opening 108 of the distal end 104 of the female coupler 100 to form a passageway along a central axis of the female coupler 100 allowing fluid communication therethrough. In an embodiment, the first inner threaded surface 106 has a thread direction configured such that the hose 300 is prevented from turning out of the female coupler 100 when the female coupler 100 and male coupler 200 are matingly engaged. In a particular embodiment, the first inner threaded surface 106 of the distal end 104 and second inner threaded surface 110 of the proximal end 102 are oppositely threaded, i.e., if the first inner threaded surface 106 is formed in a clockwise direction, the second inner threaded surface 110 would be formed in a counterclockwise direction to prevent unwanted hose turning and axial displacement.

In an embodiment, the proximal end 102 of the second inner threaded surface 110 includes a coating 114. Coating 114 is a coating that is substantially uniform on the second inner threaded surface 110. "Substantially uniform" as used herein refers to a coating 114 that has any suitable uniform thickness on the second inner threaded surface 110 to prevent galling between the female coupler 100 and the male coupler 200 when matingly connected and subsequently, disconnected. Further, the coating 114 prevents thread damage of the female coupler 100 and male coupler 200. In an embodiment, the coating 114 is desirable when the proximal end 102 of the female coupler 100 is metal. In a particular embodiment, the coating 114 is desirable when the proximal end 102 of the female coupler 100 and the male coupler 200 are metal. In an embodiment, the coating 114 has a thickness of up to about 5 mils, such as about 1 mil to about 5 mils, or even about 1 mil to about 2 mils. In an embodiment, the second inner threaded surface 110 having the coating 114 has any suitable inner diameter.

The coating 114 is typically a polymeric material that can withstand high temperatures and chemical attack. Any suitable high temperature resistant polymer is envisioned. In an embodiment, the polymer coating includes polymers that can withstand temperatures of up to about 500° F. In an embodiment, any high temperature resistant polymer approved by the FDA for fluid transport can be used. In an embodiment, the polymer is suitable for Class 3A based applications. In a particular embodiment, the polymer is polyphenylene sulfide. In an embodiment, the material is a polymer that complies with the requirements of 21 CFR 177.2490 and 21 CFR 177.2500, as classified by the FDA.

In an embodiment, the first inner threaded surface 106 receives a hose 300, where the hose 300 has an outside diameter that substantially contacts the inside diameter of the first inner threaded surface 106. In an embodiment, there is substantial interference between the outside diameter of the hose and the inside diameter of the first inner threaded surface 106 to provide a sanitary coupling assembly. "Interference" is defined as the amount that the hose outside diameter is greater than the inside diameter of the first inner threaded surface 106. In a particular embodiment, the interference between the outside diameter of the hose 300 and the inner diameter of the first inner threaded surface 106 is at least about 0.030 inches and up to at least about 0.090 inches.

In an example, a singular female coupler 100 having an interference between the outside diameter of the hose 300 and the inner diameter of the first inner threaded surface 106 of at least about 0.030 inches and up to at least about 0.090 inches has beneficial physical attributes. The female coupler 100 can be assembled with a number of hoses 300 of the same type and inner diameter size, regardless of outside diameter variations of the hose 300. Multiple female couplers 100 are not needed for a range of hoses 300 having a variable inner diameter with a range of outside diameters. In an embodiment, the hose 300 has an inner diameter of about 2 inches and the first inner threaded surface 106 has nominal number of threads of about 3 threads per inch (TPI). In an embodiment, the first inner threaded surface 106 has a number of threads of about 1 thread per inch to about 7 threads per inch, or even greater than 7 threads per inch, wherein the hose 300 may have any suitable inner diameter. Typically, the number of threads per inch is dependent upon the inner diameter of the hose 300. Further, the threading pattern of the first inner threaded surface 106 maintains a sanitary seal between the female coupler 100 and the hose 300.

In an embodiment, the first inner threaded surface 106 has a relatively thin razor-like edge 116 which extends diagonally inward toward a central axis and the proximal end 102 and into the axial region defined by the opening 108. At an interface of the first inner threaded surface 106 and the second inner threaded surface 110 is a hose seat 118. After the female coupler 100 has been properly threaded onto the hose 300, the hose end 302 abuts the hose seat 118.

Male coupler 200 includes a proximal end 202 and a distal end 204. As stated earlier, the proximal end 102 of the female coupler 100 includes the second inner threaded surface 110 that is configured to matingly engage the male coupler 200. In an embodiment, the female coupler 100 has an inside diameter and the male coupler 200 has an outside diameter wherein the inside diameter of the female housing 100 is greater than the outside diameter of the male coupler 200 to provide a frictional fit. Typically, proximal end 202 of male coupler 200 is tapered having a terminal end 206 that is slightly less diameter than the inner diameter of the hose 300 and an intermediate portion 208 of slightly larger diameter than the inner diameter of the hose 300. The tapered design of the proximal end 202 allows for easy acceptance and position of the male coupler 200 into the inner diameter of the hose 300 while providing radially outward pressure on the inner surface of the hose 300 to lend to a frictional fit of the male coupler 200 with the hose 300.

Figure 1:
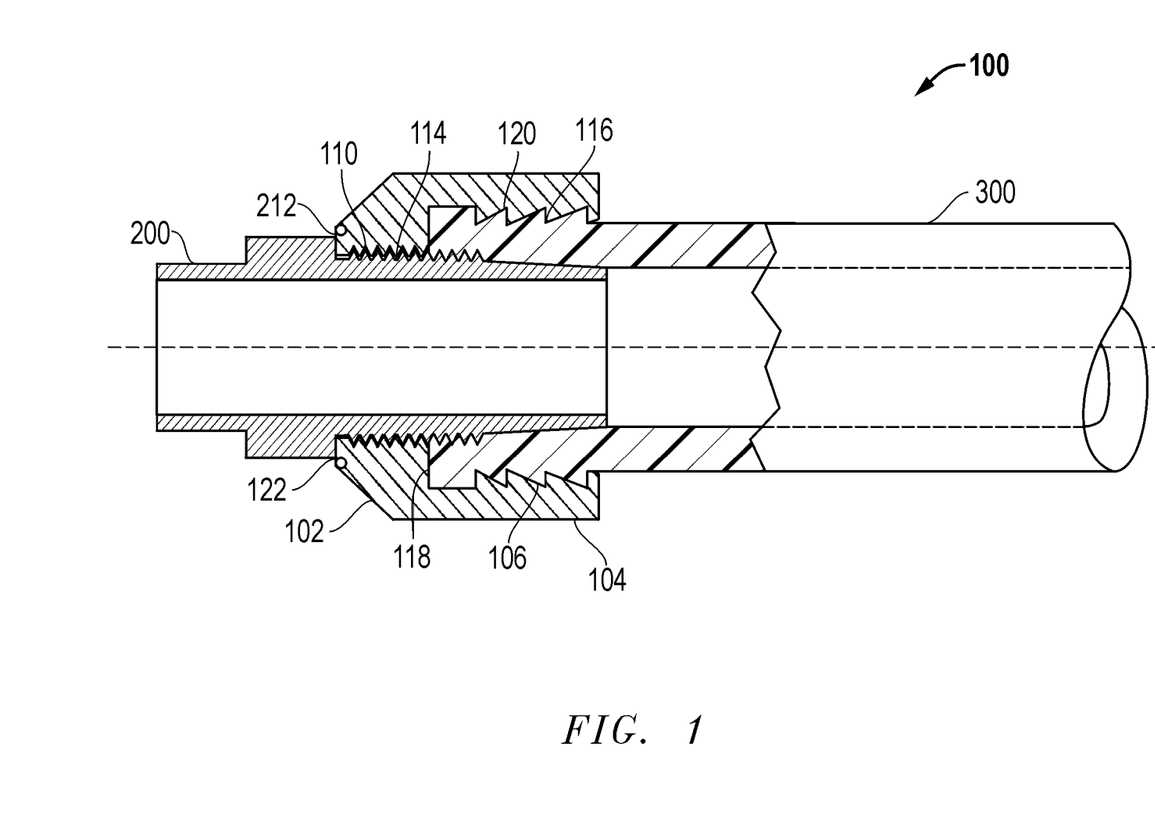
FIGS. 1, 2, and 3 include illustrations of an exemplary coupling assembly.
Figure 2:
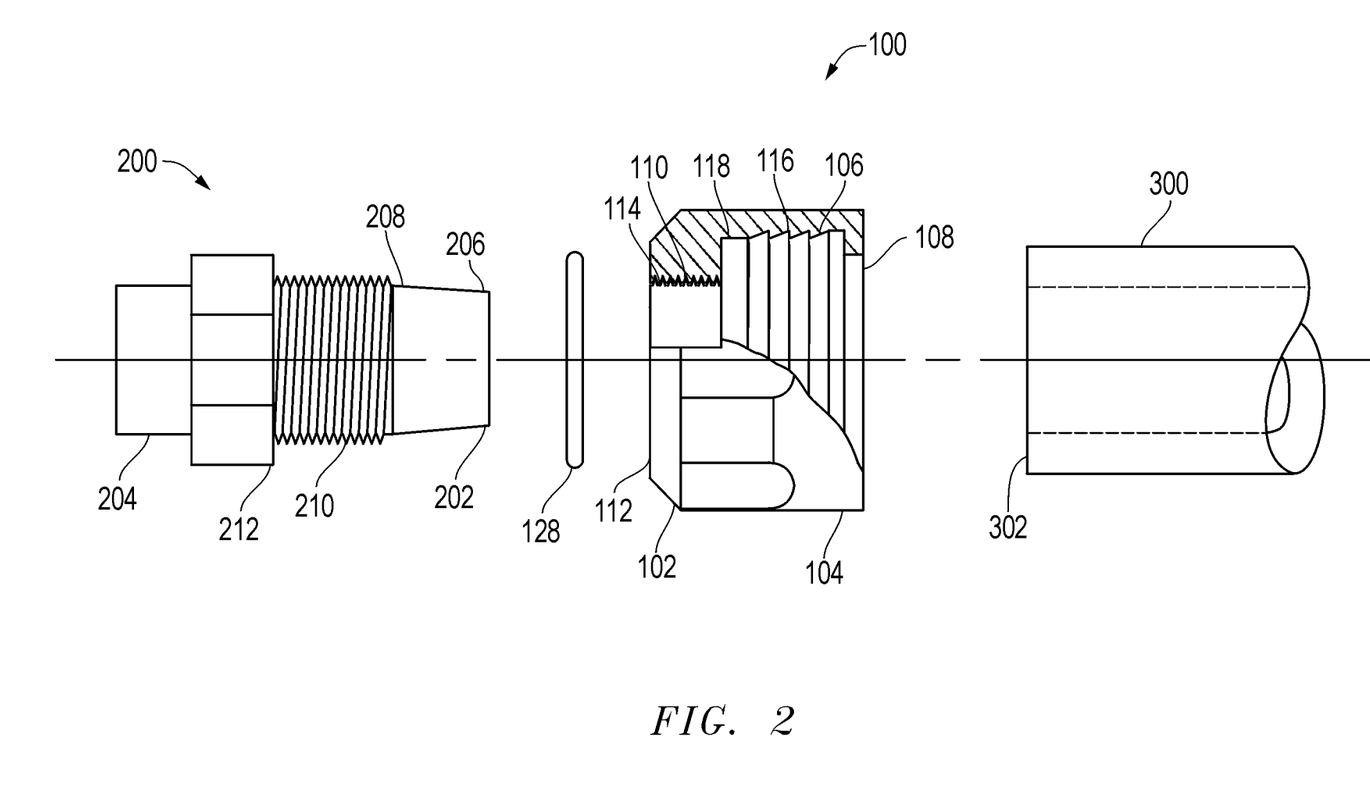

As seen in FIG. 1, a seal is provided when female coupler 100 and male coupler 200 matingly engage. With complete insertion of the proximal end 202 of the male coupler 200 into the female coupler 100, the male coupler 200 engages the inner diameter of the hose 300. The proximal end 202 of the male coupler 200 forces the hose 300 against the first inner threaded surface 106 of the female coupler 100. At least a portion of the outer surface of the hose 300 is forced into a substantially tight frictional fit into grooves 120 of the first inner threaded surface 106, forming a slight serpentine-like protruded area. The proximal end 202 of male coupler 200 not only forces the hose 300 into the first inner threaded surface 106, but also creates a sealing interface between the female coupler 100 and the inner diameter of the hose wall. A lock is further created between the hose 300 within the female coupler 100 to prevent axial and distal displacement of the hose 300 from the female coupler 100.

The intermediate portion 208 has an external threaded surface 210 formed in a complementary manner to second inner threaded surface 110 of female coupler 100 allowing threaded connection thereof. In a particular embodiment, the female coupler 100 and male coupler 200, when engaged, define a generally hollow body having an interior surface, defining a lumen for fluid flow therethrough to connect the distal ends of couplers 100 and 200, such as a fluid passage between the couplers 100 and 200. Disposed adjacent to the threaded surface 210 and axially further displaced from the proximal end 202 is a radially extending shoulder 212. Distal end 204 of male coupler 200 is formed in a manner to be readily connected to any suitable fixture used in the sanitary transport industry. Any suitable standard sanitary end is envisioned. In an embodiment, a standard end includes, for example, Tri-Clamp® by Laddish Co., Wisconsin or I-Line and Q-Line by Cherry Burrell, Iowa. The standard end may be formed in any suitable manner such as by welding to the distal end 204. The male coupler 200 may then be connected to any suitable sanitary equipment such as receiving pumps, processing equipment, storage vats, transport trucks, and the like.

Figure 3:
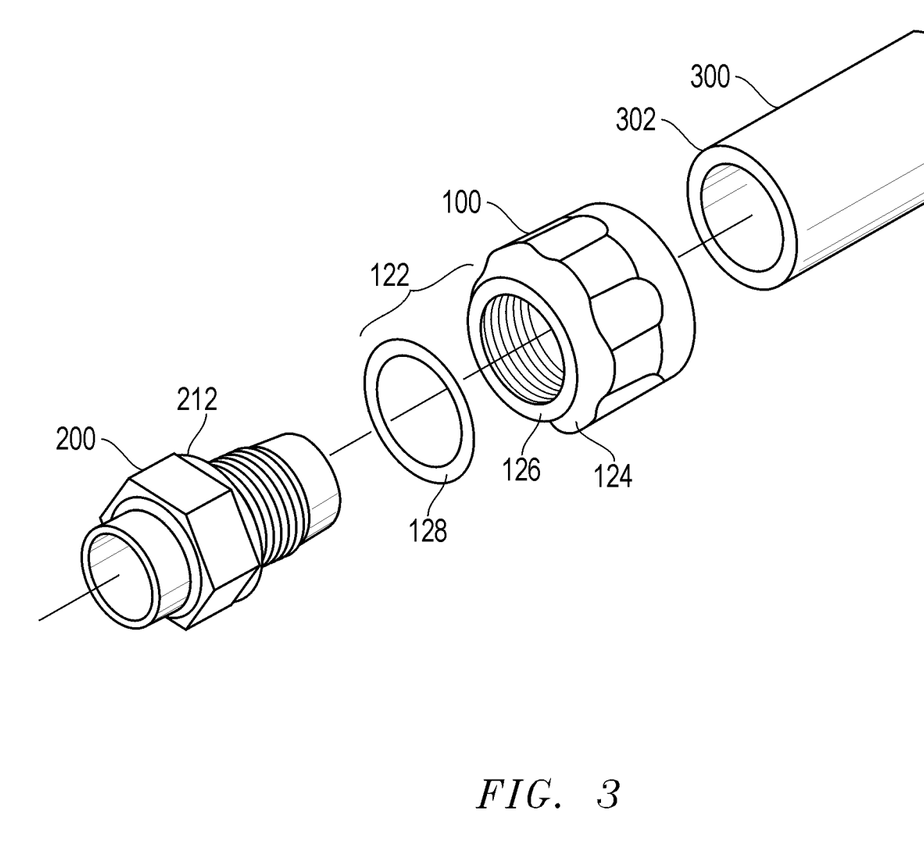

In an embodiment and as best seen in FIG. 3, the proximal end 102 of the female coupler 100 may include a seal structure 122. Any suitable seal structure 122 is envisioned. For instance, the proximal end 102 of the female coupler 100 includes a collar 124 that includes an annular groove 126 therein. In a particular embodiment, the annular groove 126 includes a seal 128 that may be continuous and may completely engage the male coupler 200 to form a sanitary connection. The seal 128 may be formed of any suitable material, which precludes the passage of contaminants. For example, the seal 128 may be an O-ring. In an embodiment, the seal 128 may be made of any material approved by the FDA for fluid transport. In an exemplary embodiment, the seal 128 may be formed of a polymeric material. An example polymeric material includes an elastomer, such as a silicone elastomer, thermoplastic elastomer, thermoplastic vulcanizate, or polymer containing ethylene propylene diene monomer. The seal 128 may also be treated with an antibacterial compound or contain an antibacterial layer.

The male coupler 200 is dimensioned to form a tight frictional fit between the seal structure 122 and the male coupler 200 when the male coupler 200 and female coupler 100 are matingly engaged. In a particular embodiment, the shoulder 212 engages the seal structure 122 in a tight frictional fit to maintain a sanitary environment within the coupling assembly (100 and 200) when engaged. For instance, the shoulder 212 engages the O-ring 128 when the female coupler 100 and the male coupler 200 are matingly engaged in a threaded fashion. In the assembled form of the sanitary coupling assembly as seen in FIG. 1, the shoulder 212 engages the O-ring 128 against the collar 124. At least a portion of the seal structure 122 and the O-ring 128 are protruding and exposed to provide the benefit of visually inspecting the seal structure 122 and preventing any contaminants from entering the junction between the female coupler 100 and the male coupler 200.

The coupler assembly (100 and 200) may be made of any material that is compatible with the nature of the particular fluid or sterilization technique utilized. In an embodiment, at least a portion of the coupling assembly is made of any material approved by the FDA for fluid transport. In an exemplary embodiment, the materials may be metal, such as stainless steel. In another embodiment, the materials may be polymers, such as USP ADCF (animal derived component free) materials and USP Class VI/ADCF materials. In an embodiment, the polymers may be polyvinylidene fluoride (PVDF) or polypropylene. In an embodiment, the female coupler 100 and the male coupler 200 may be made of the same or different materials. Further, the couplers may include independent, multiple components or continuous, integral components.

The distal ends of each coupler 104 and 204 may be configured to engage a fluid system. The couplers 100 and 200 can be made in a variety of suitable sizes. In an embodiment, the distal ends 104 and 204 of the female coupler 100 and male coupler 200 are configured with any suitable outside diameter envisioned. In a particular embodiment, the distal ends 104 and 204 of the couplers 100 and 200 have an inside diameter of up to about 4 inches.

Further, the hose 300 may have any suitable diameter envisioned. As stated earlier, the interference between the outside diameter of the hose 300 and the inside diameter of the distal end 104 of first inner threaded surface 106 allows for coupling of the female coupler 100 to the hose 300 with a range of outside diameter variations. In an embodiment, the hose can be any suitable hose used for transferring products, which must remain substantially sanitary. In a particular embodiment, the hose may be any suitable flexible, non-metallic hose. In an example, the hose may be a rubber-based hose, PVC hose, Teflon-lined hose, silicone hose, and the like.

Figure 4:
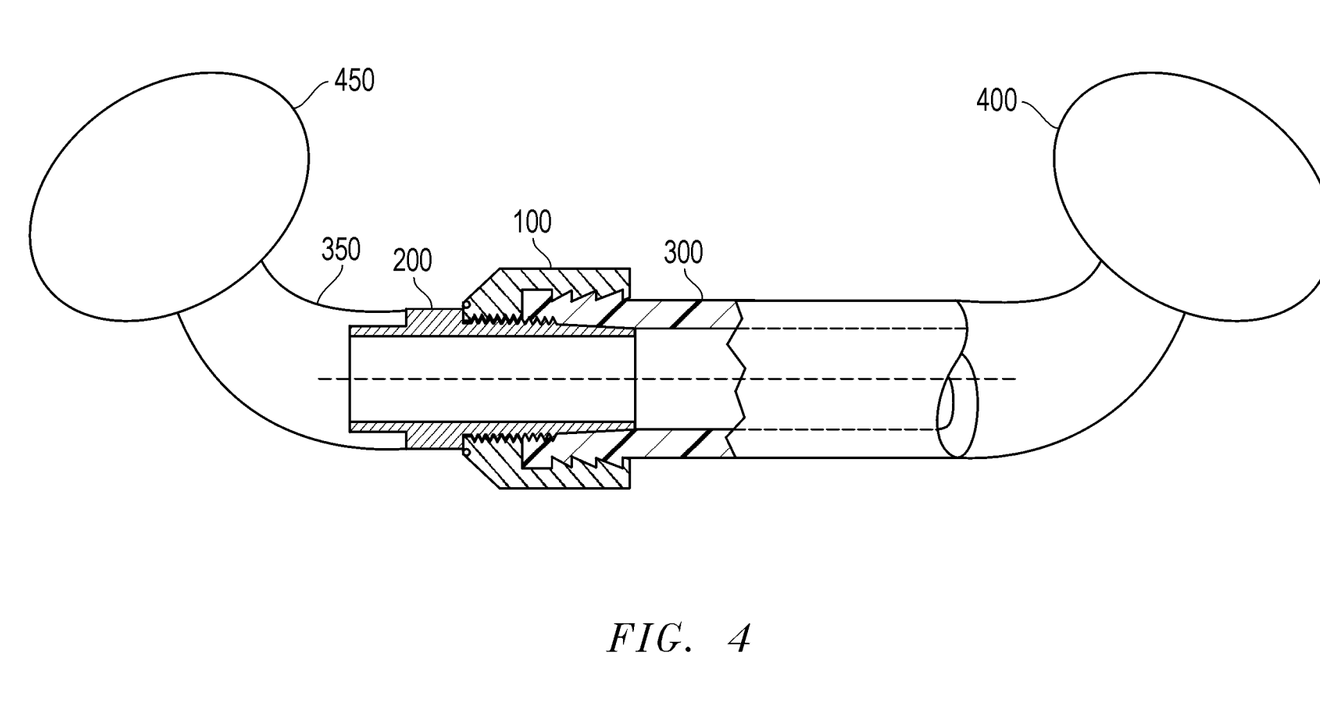
FIG. 4 includes an illustration of an exemplary assembly including an exemplary coupling assembly.

Each coupler may be attached to or may be formed as part of any suitable fluid container or conduit. FIG. 4 includes an illustration of an exemplary fluid system in which a container 400 is fluidly coupled to a container 450. The container 400 is coupled through a hose 300 coupled to a female coupler 100 that is coupled to a male coupler 200, which is coupled to a hose 350 that is coupled to the container 450. As stated earlier, distal end 204 of male coupler 200 is formed in a manner to be readily connected to any suitable fixture used in the sanitary transport industry. In particular, the coupling assembly may be suitable for fluid communication where the pressure rating is greater than or equal to about 600 psi.

In an exemplary embodiment, the coupling assembly is suitable for sterilization. In an embodiment, the couplers may be sterilized by radiation sterilization or heat sterilization. In particular, the materials of the couplers may be selected based on the anticipated method of sterilization. Particularly, the coupling assembly may be configured for sterilization in an autoclave at temperatures of about 134° C. at 17 psi for about 1 hour. Alternatively, the coupling assembly may be configured for sterilization by radiation using gamma rays at 25 kGy for 2 doses. Further, the coupling assembly may be packaged to maintain sterilization.

In an exemplary embodiment, operation of the couplers 100 and 200 includes matingly engaging the opening 108 of female coupler 100 to the hose end 302 and rotating to axially move the hose end 302 into the first inner threaded surface 106 of female housing 100. The outer surface of the end 302 of the hose is threadly cut by the edge 116 of the first inner threaded surface 106. The hose 300 is threaded axially to engage the hose end 302 with the hose seat 118. Thus, a fine complimentary groove (not shown) is formed in the outer surface of the hose 300. The complimentary groove is sufficiently deep such that when threaded together with the first inner threaded surface 106, the hose 300 is prevented from axially moving in the distal direction and outside of the female coupler 100. The depth of the complimentary groove, however, does not comprise the integrity of the hose.

In an embodiment, the O-ring 128 is place in the annular groove 126 of the female coupler 100 and maintained therein prior to inserting the male coupler 200 into the female coupler 100. Female coupler 100 is positioned to receive the proximal end 202 of the male coupler 200 in the opening 112. Male coupler 200 is rotated to be threadedly drawn axially into female coupler 100. As male coupler 200 is threaded into female coupler 100, the proximal end 202 pushes the hose 300 into the first inner threaded surface 106 of female coupler 100. Further, as male coupler 200 is threaded into female coupler 200, the shoulder 212 nears and ultimately abuts the O-ring 128 of the sealing structure 122. At this point, it is found desirable to further thread male coupler 200 into female coupler 100 until sufficient resistance builds at the interface between the shoulder 212, O-ring 128, and collar 124 to substantially secure male coupler 200 in place and prevent rotational and axial movement of male coupler 200 with respect to female coupler 100. This further threading can result in a slight bulging of the O-ring 128. The junction formed by the interconnection of the shoulder 212, O-ring 128, and collar 124 maintains a visible and highly suitable seal against leakage, bacteria, and contaminants to provide a sanitary transfer of product. The sanitary and sterile connection is complete.

In particular, the sanitary coupling assembly 100 and 200 may provide advantages over other sanitary connectors. For example, the coating 114 on the second inner threaded surface 110 provides a surface that allows the sanitary coupling assembly to be used a multiple number of times, i.e. reusable. Further, the coating prevents both galling and thread damage. In an embodiment, the coating 114 is configured such that a polymer sleeve insert (not shown) is not needed.

Further, the threading pattern on the first inner threaded surface 106 provides a female coupler 100 that can be coupled to any number of hoses having a variable inner diameter and a range of outside diameters. In a particular embodiment, the threading pattern maintains a sanitary environment for the transfer of fluids.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A sanitary assembly comprising:
   a hose having an outside diameter,
   a distal end having a first inner threaded surface defining an opening therein having a uniform inner diameter, wherein the first inner threaded surface has a number of threads of about 1 thread per inch to about 3 threads per inch (TPI) and is capable of being coupled to any number of hoses having a variable inner diameter and a range of outside diameters, wherein the distal end is adapted to connect to a hose, the hose having an outside diameter, wherein the outside diameter of the hose is greater than the inner diameter of the first inner threaded surface by at least 0.030 inches and up to at least about 0.090 inches; and
   a proximal end having a second inner threaded surface, said second inner threaded surface having a polymer coating, wherein the polymer coating includes a single polymer material and includes a thickness of 1 mil to 5 mils and wherein the proximal end is configured to matingly engage a complementary structure located on a complementary coupler without thread galling.

2. The sanitary assembly of claim 1, wherein the proximal end is metal.

3. The sanitary assembly of claim 2, wherein the metal is stainless steel.

4. The sanitary assembly of claim 1, wherein the polymer coating comprises a high temperature polymer resistant to temperatures of up to about 500° F.

5. The sanitary assembly of claim 4, wherein the high temperature polymer is polyphenylene sulfide (PPS).

6. The sanitary assembly of claim 1, wherein the second inner threaded surface defines an opening adjacent and coaxial with the opening of the distal end to form a passageway along a central axis of the coupler allowing fluid communication therethrough.

7. The sanitary assembly of claim 1, wherein the proximal end further includes a seal structure configured to engage a shoulder of the complementary coupler after the coupler and the complementary coupler matingly engage.

8. The sanitary assembly of claim 7, wherein the seal structure includes a collar with an annular grooved surface therein and an O-ring disposed within the grooved surface.

9. The sanitary assembly of claim 1, wherein the complementary coupler is metal.

10. The sanitary assembly of claim 1, wherein the coupler is reusable.

11. A sanitary assembly comprising:
    a hose; and
    a sanitary coupler comprising a distal end having a first inner threaded surface defining an opening therein having a uniform inner diameter, wherein the first inner threaded surface has a number of threads of about 1 thread per inch to about 3 threads per inch (TPI) providing an inner surface coupled to the hose, wherein an interference between an outer diameter of the hose and an inner diameter of the first inner threaded surface is at least about 0.030 inches and up to at least about 0.090 inches; and
    a proximal end having a second inner threaded surface, the second inner threaded surface being configured to matingly engage a complementary structure located on a complementary coupler.

12. The sanitary assembly of claim 11, wherein the distal end is configured to receive a hose having an inside diameter of up to about 4 inches.

13. The sanitary assembly of claim 11, wherein the first inner threaded surface has a nominal number of threads of about 3 threads per inch (TPI).

14. The sanitary assembly of claim 13, wherein the inside diameter is about 2 inches.

15. The sanitary assembly of claim 11, wherein the second inner threaded surface defines an opening adjacent and coaxial with the opening of the distal end to form a passageway along a central axis of the coupler allowing fluid communication therethrough.

16. The sanitary assembly of claim 11, wherein the proximal end further includes a seal structure configured to engage a shoulder of the complementary coupler after the coupler and complementary coupler matingly engage.

17. The sanitary assembly of claim 16, wherein the seal structure includes a collar with an annular grooved surface therein and an O-ring disposed within the grooved surface.

18. The sanitary assembly of claim 11, wherein the coupler is reusable.

19. A sanitary coupling assembly comprising:
a hose having an outside diameter;
a male coupler having an external threaded surface; and
a female coupler having a proximal end and a distal end, the distal end having a first inner threaded surface defining an opening therein having a uniform inner diameter, wherein the outside diameter of the hose is greater than the inner diameter of the first inner threaded surface by at least 0.030 inches and up to at least about 0.090 inches, wherein the proximal end of the female coupler includes a second inner threaded surface coated with a polymer and the second inner threaded surface of the female coupler is configured to engage the external threaded surface of the male coupler.

* * * * *